(12) United States Patent
Pollen et al.

(10) Patent No.: US 9,919,084 B2
(45) Date of Patent: Mar. 20, 2018

(54) VACUUM BREAK BACKFLOW PREVENTER FOR BREAST PUMP SYSTEMS

(71) Applicants: Ashia M. Pollen, Madison, WI (US); Robert J. Harter, La Crosse, WI (US)

(72) Inventors: Ashia M. Pollen, Madison, WI (US); Robert J. Harter, La Crosse, WI (US)

( * ) Notice: Subject to any disclaimer, the term of this patent is extended or adjusted under 35 U.S.C. 154(b) by 478 days.

(21) Appl. No.: 14/685,663

(22) Filed: Apr. 14, 2015

(65) Prior Publication Data

US 2015/0217034 A1     Aug. 6, 2015

(51) Int. Cl.
*A61M 1/06* (2006.01)
*A61M 1/00* (2006.01)

(52) U.S. Cl.
CPC ............ *A61M 1/06* (2013.01); *A61M 1/0049* (2013.01); *A61M 1/062* (2014.02); *A61M 1/064* (2014.02); *A61M 1/066* (2014.02)

(58) Field of Classification Search
CPC ......... A61M 1/06; A61M 1/062; A61M 1/064
See application file for complete search history.

(56) References Cited

U.S. PATENT DOCUMENTS

| | | | |
|---|---|---|---|
| 155,720 | A | 10/1874 | Gray |
| 684,078 | A | 10/1901 | Martin |
| 3,840,012 | A | 10/1974 | Rushton, Jr. |
| 4,263,912 | A | 4/1981 | Adams |
| 4,270,538 | A | 6/1981 | Murphy |
| 4,425,935 | A | 1/1984 | Gonzalez |
| 4,582,073 | A | 4/1986 | Simkanich |
| 4,673,388 | A | 6/1987 | Schlensog et al. |
| 4,857,051 | A | 8/1989 | Larsson |
| 4,892,517 | A | 1/1990 | Yuan et al. |
| 4,929,229 | A | 5/1990 | Larsson |
| 5,009,638 | A | 4/1991 | Riedweg et al. |
| 5,071,403 | A | 12/1991 | Larsson |
| 5,295,957 | A | 3/1994 | Aida et al. |
| 5,358,476 | A | 10/1994 | Wilson |
| 5,571,084 | A | 11/1996 | Palmer |
| 5,720,722 | A | 2/1998 | Lockridge |
| 5,941,847 | A | 8/1999 | Huber et al. |
| 5,954,690 | A | 9/1999 | Larsson |
| 6,004,186 | A | 12/1999 | Penny |

(Continued)

*Primary Examiner* — Nathan R Price
*Assistant Examiner* — Melissa A Snyder
(74) *Attorney, Agent, or Firm* — bobharter.com; Robert J. Harter

(57) ABSTRACT

A breast pump system includes a vacuum break backflow preventer for preventing breast milk from accidentally backflowing into a suction tube leading to a vacuum pump. The backflow preventer is a vacuum passageway with two spaced apart suction openings. The two openings convey air to cyclically pressurize and depressurize a small milk charging chamber. If milk accidentally covers one of the openings, air at the other opening minimizes the pressure differential that might otherwise draw the milk deep into the suction tube and toward the vacuum pump. For ease of cleaning and sanitizing, the system avoids or minimizes the use of baffles, permanently enclosed passageways, moving parts, and tight inside corners. Some passageways can be split open for access during cleaning. To make the breast milk collection device less protruding under a brassier, the vacuum passageway curves around the side of a nipple receptacle rather than in front of it.

23 Claims, 14 Drawing Sheets

(56) References Cited

U.S. PATENT DOCUMENTS

| | | |
|---|---|---|
| 6,379,327 B2 | 4/2002 | Lundy |
| 6,440,100 B1 | 8/2002 | Prentiss |
| 6,575,202 B2 | 6/2003 | Lafond |
| 6,652,484 B1 | 11/2003 | Hunckler et al. |
| 6,706,012 B2 | 3/2004 | McKendry et al. |
| 6,764,377 B2 | 7/2004 | Gillan |
| 6,821,185 B1 | 11/2004 | Francis |
| 6,866,558 B2 | 3/2005 | Luciano et al. |
| 6,887,217 B1 | 5/2005 | Logan |
| 6,974,361 B2 | 12/2005 | Cravaack et al. |
| 7,094,217 B2 | 8/2006 | Fialkoff |
| 7,128,877 B2 | 10/2006 | Quay et al. |
| 7,223,255 B2 | 5/2007 | Myers et al. |
| 7,559,915 B2 | 7/2009 | Dao et al. |
| 8,075,516 B2 | 12/2011 | Pfenniger et al. |
| 8,118,772 B2 | 2/2012 | Dao et al. |
| 8,414,353 B1 | 4/2013 | Leavell |
| 8,529,501 B2 | 9/2013 | Wach et al. |
| 8,568,350 B2 | 10/2013 | Schlienger et al. |
| 8,702,646 B2 | 4/2014 | Garbez et al. |
| 8,801,495 B1 | 8/2014 | Guindon |
| 2014/0052056 A1* | 2/2014 | Garbez ............... A61M 1/062 604/74 |

\* cited by examiner

FIG. 9
FIG. 10
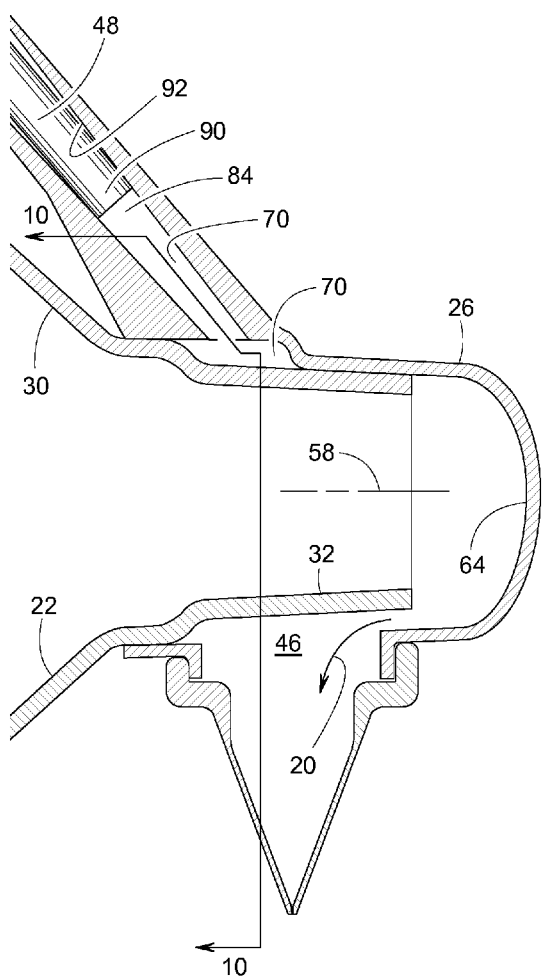
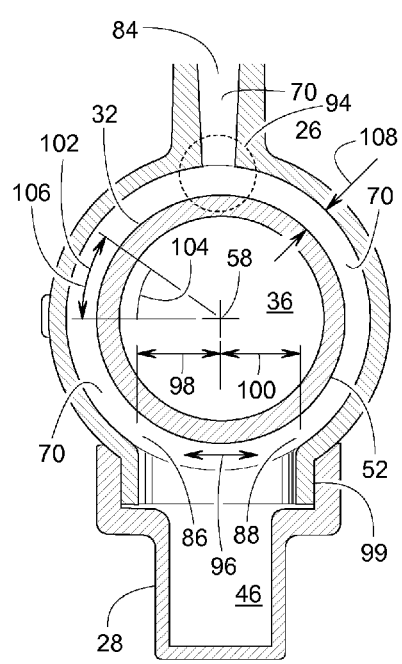

FIG. 11
FIG. 12
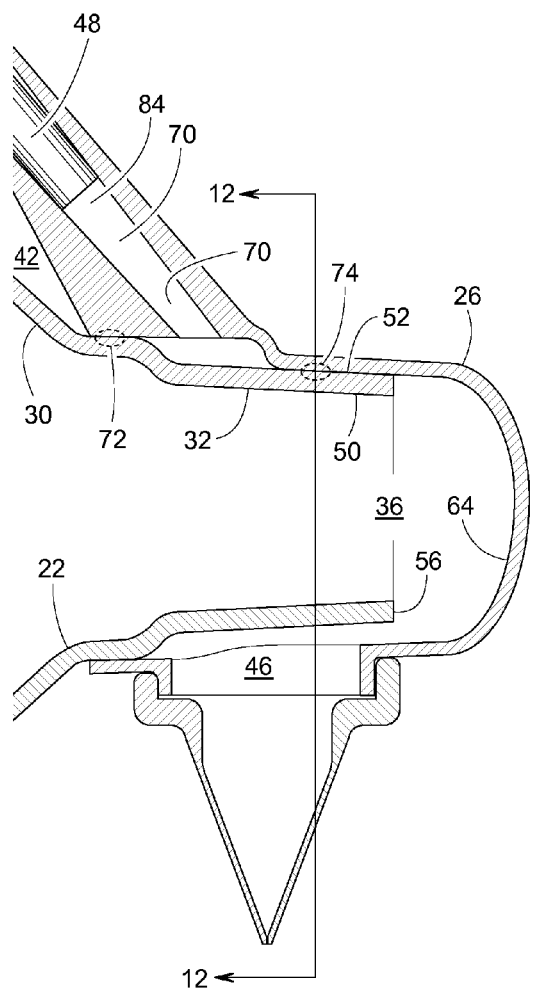
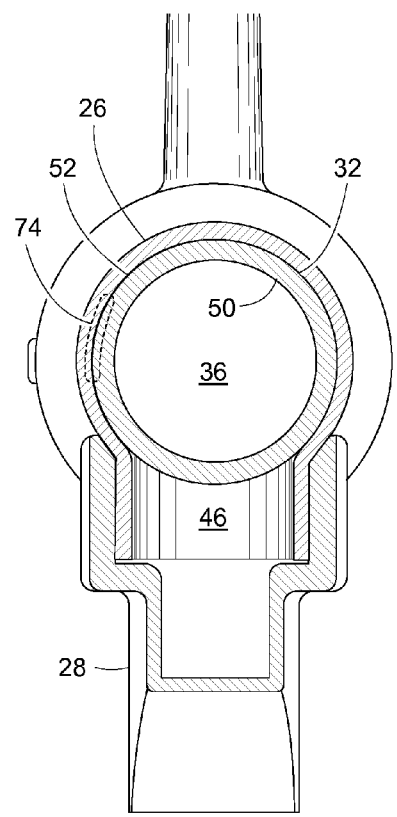

FIG. 13
FIG. 14
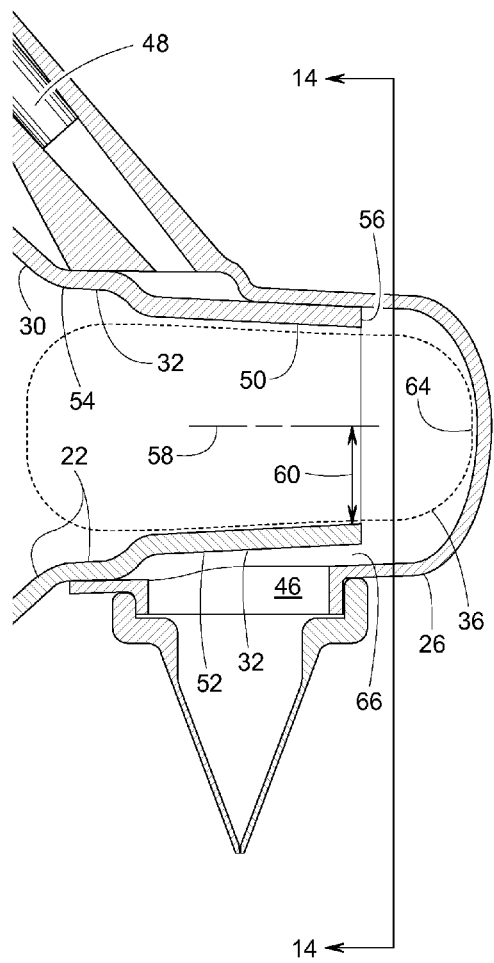
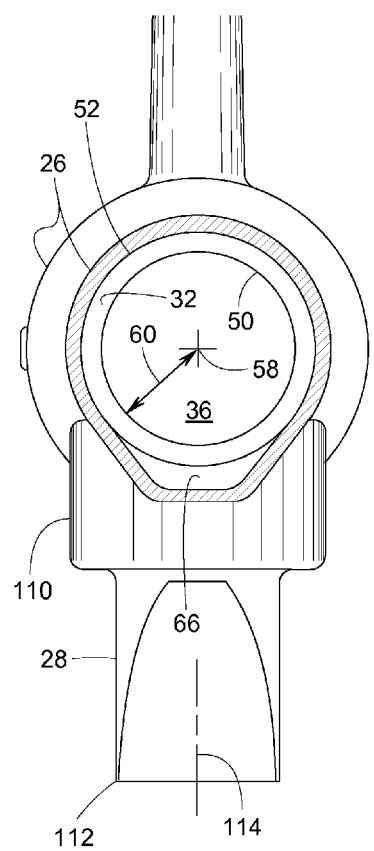

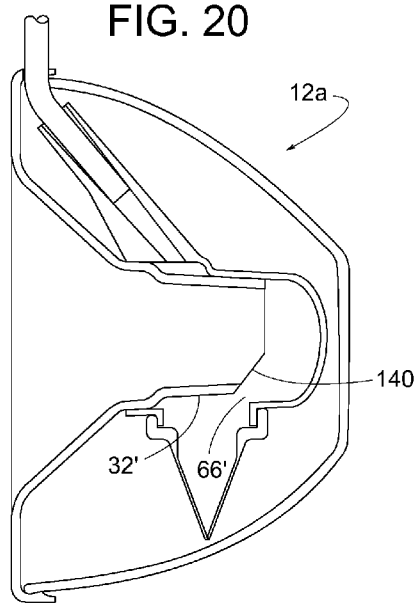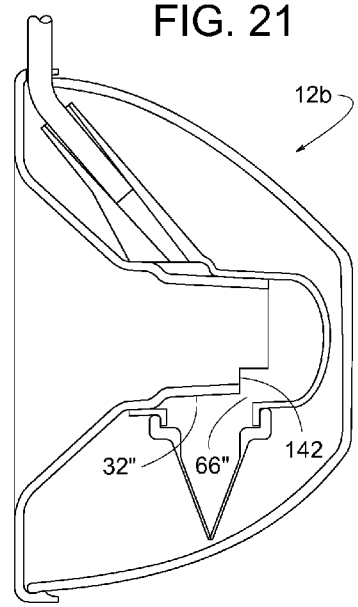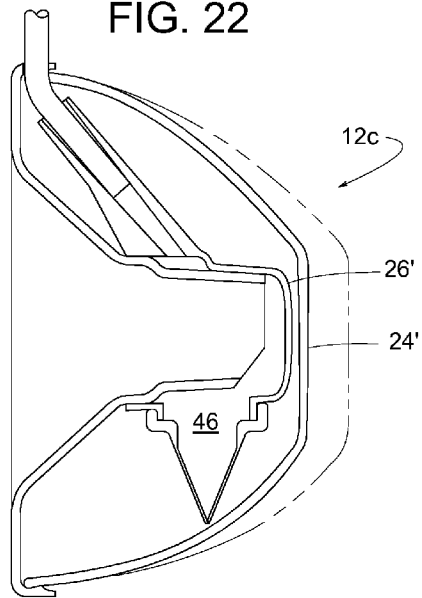

VACUUM BREAK BACKFLOW PREVENTER FOR BREAST PUMP SYSTEMS

FIELD OF THE DISCLOSURE

The subject invention generally pertains to human breast milk collection systems and more specifically to means for inhibiting milk from backflowing through a suction tube leading to a vacuum pump.

BACKGROUND

Breast pump systems are used for collecting breast milk expressed from a lactating woman. Some breast pump systems have a milk collection device with a funnel that fittingly receives the woman's breast. In many cases, a vacuum pump provides cyclical periods of positive and negative pressure to the milk collection device. During periods of negative pressure (subatmospheric pressure), vacuum delivered to the device withdraws a small discrete volume of milk from the breast and conveys that charge of milk to a small charging chamber. During each period of positive pressure, lightly pressurized air relaxes the breast momentarily and at the same time forces the charge of milk from the charging chamber to a larger milk storage chamber. The cycle repeats until the storage chamber is full or the woman is finished "pumping."

Some breast pump systems have a milk collection device that is worn within the cup of a common brassiere. Examples of such systems are disclosed in U.S. Pat. Nos. 7,559,915; 8,118,772; and 8,702,646; all of which are incorporated herein by reference

BRIEF DESCRIPTION OF THE DRAWINGS

FIG. 9 is a cross-sectional view showing a portion of FIG. 6.

FIG. 10 is a cross-sectional view taken along line 10-10 of FIG. 9.

FIG. 11 is a cross-sectional view showing a portion of FIG. 6.

FIG. 12 is a cross-sectional view taken along line 12-12 of FIG. 11.

FIG. 13 is a cross-sectional view showing a portion of FIG. 6.

FIG. 14 is a cross-sectional view taken along line 14-14 of FIG. 13.

FIG. 20 is a cross-sectional view similar to FIG. 1 but showing another example milk collection device constructed in accordance with the teachings disclosed herein.

FIG. 21 is a cross-sectional view similar to FIG. 1 but showing another example milk collection device constructed in accordance with the teachings disclosed herein.

FIG. 22 is a cross-sectional view similar to FIG. 1 but showing of another example milk collection device constructed in accordance with the teachings disclosed herein.

DETAILED DESCRIPTION

Figure 17:
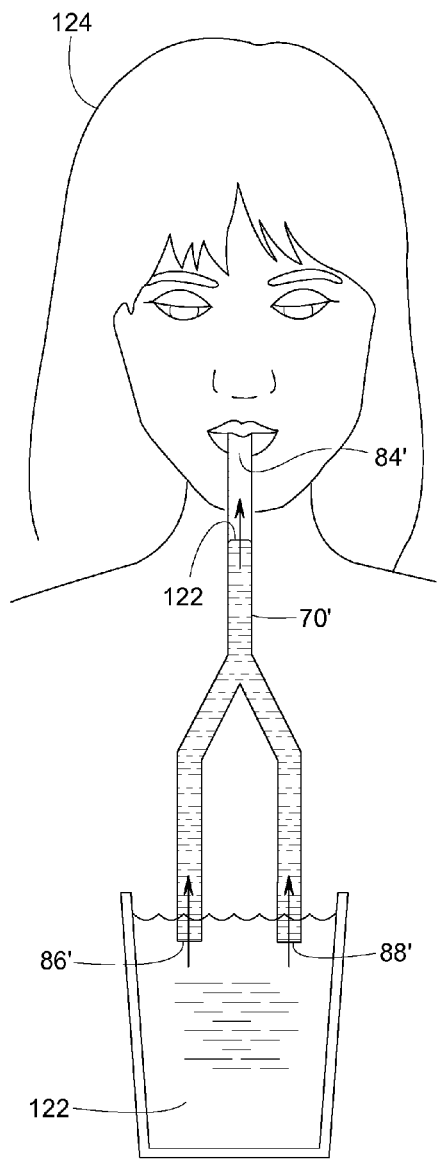
FIGS. 17 and 18 are illustrations demonstrating an example "vacuum break" concept.
Figure 18:
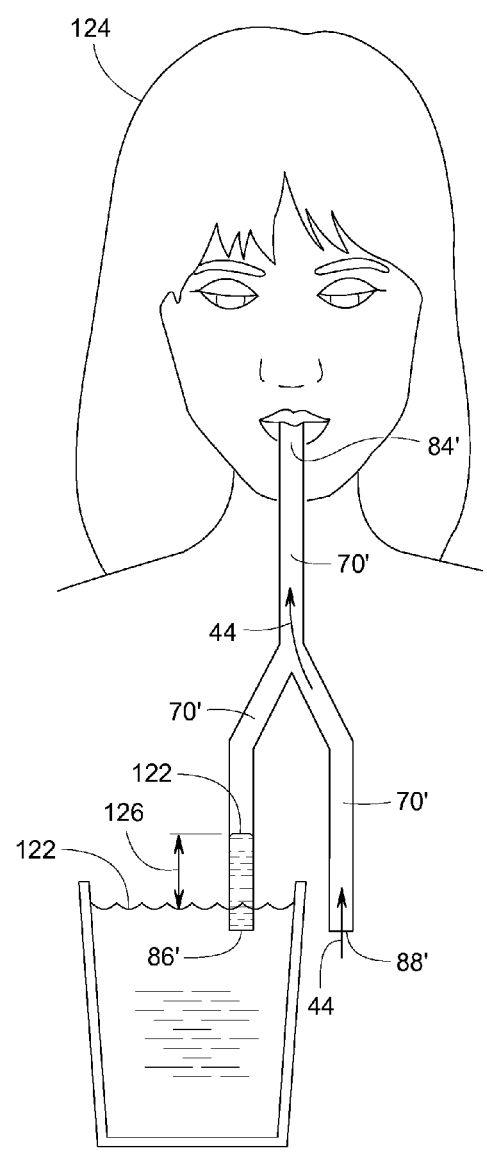
Figure 19:
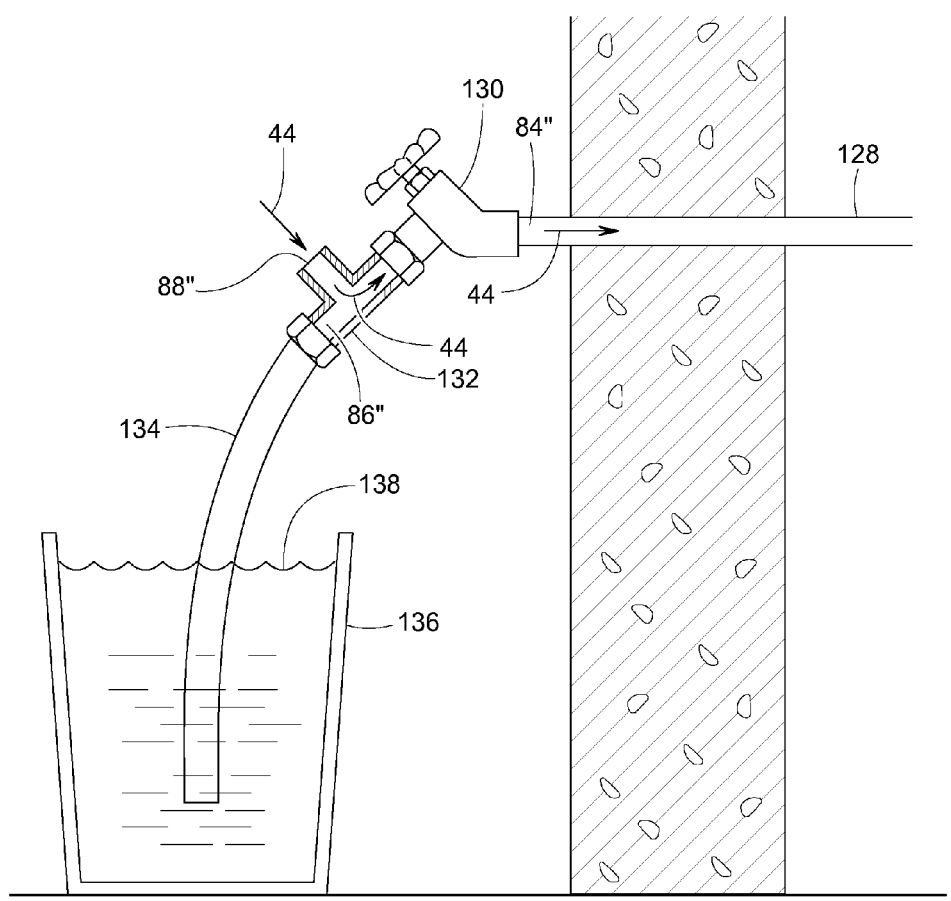
FIG. 19 is an illustration demonstrating another example "vacuum break" concept.

FIGS. 1-16 show various views of an example breast pump system 10 that includes a milk collection device 12 with means for preventing milk 14 from backflowing to a vacuum pump 16. FIGS. 17-19 illustrate the underlying operating principle of vacuum breakers. And FIGS. 21-22 show variations of the system design. The general design isolates a subatmospheric air flow path 102 (FIG. 10) from a milk flow path 20 (FIG. 9) even if milk collection device 12 it tipped completely over (FIG. 4). The vacuum breaker concept keeps fluids separated without using conventional baffles, which inherently have crevices that can be difficult to clean.

Figure 1:
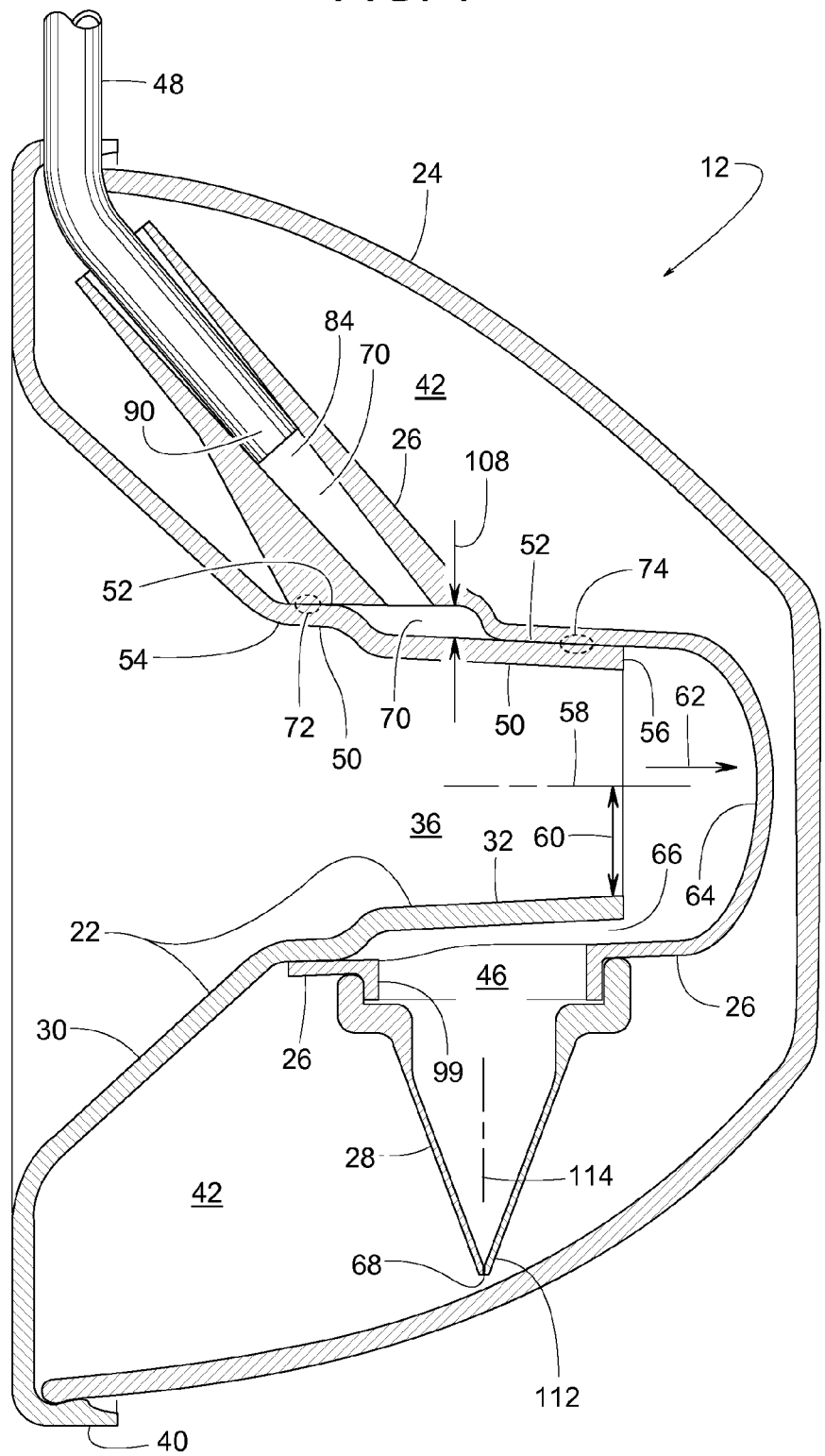
FIG. 1 is a cross-sectional side view of an example milk collection device constructed in accordance with the teachings disclosed herein.
Figure 5:
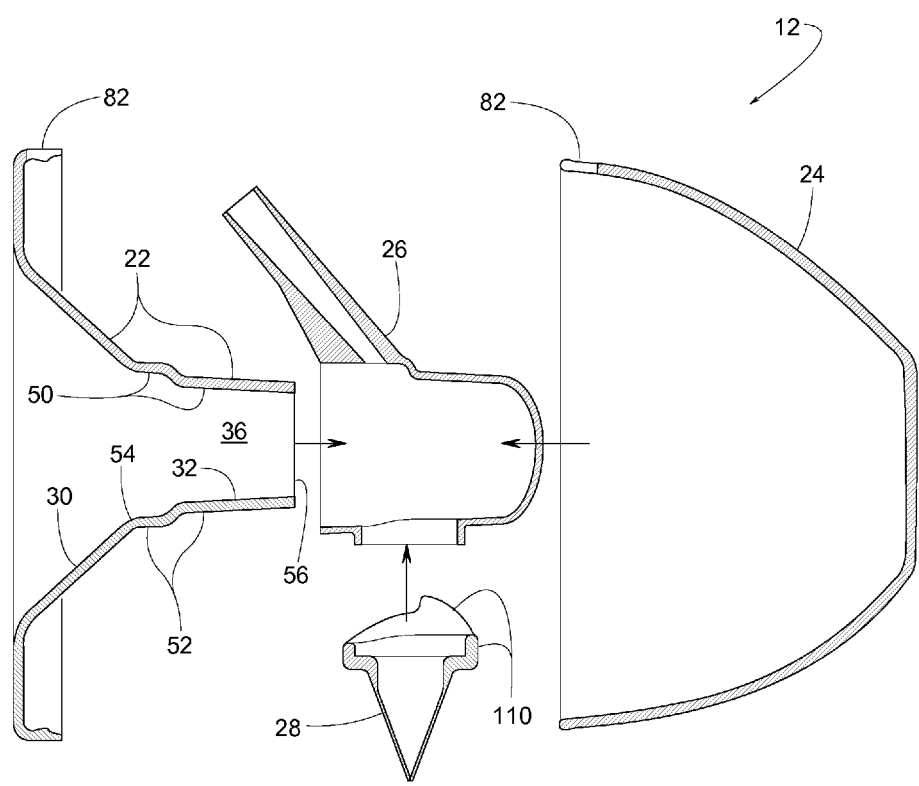
FIG. 5 is a cross-sectional view of the milk collection device shown in FIG. 1 but showing the device in a disassembled cleaning state.

As an overview of the breast pump system's general construction, milk collection device 12 comprises four main parts: a funnel-shaped breast receiver 22, a domed outer shell 24, a fluid exchanger 26, and a unidirectional valve 28 (e.g., a check valve, a duckbill check valve, a reed valve, a ball check valve, a diaphragm check valve, a swing check valve, etc.). FIG. 1 shows these for main parts in an assembled operating state with the parts being positioned as a unit in a predetermined orientation, and FIG. 5 shows them in a disassembled cleaning state. Breast receiver 22 itself comprises a breast guide 30 and a nipple receptacle 32. Breast guide 30 is generally conical for fittingly receiving a breast 34 of a lactating woman 37, and nipple receptacle 32 is tubular and defines a nipple chamber 36 for receiving a nipple 38 of breast 34.

In some examples, outer shell 24 removably connects to a flange 40 of breast receiver 22 to define a milk storage chamber 42 between outer shell 24 and breast receiver 22. Fluid exchanger 26 is coupled to breast receiver 22 to provide means for strategically directing milk 14 and air 44 within milk collection device 12. Valve 28 establishes a milk charging chamber 46 between nipple receptacle 32 and storage chamber 42. In some examples, charging chamber 46 is cycled between positive and negative pressure to draw discrete quantities of expressed milk from nipple receptacle 32. During periods of positive pressure, charging chamber 46 discharges each discrete quantity or charge through valve 28 to storage chamber 42.

To provide charging chamber 46 with air 44 cyclically at subatmospheric pressure and positive or atmospheric pressure, a suction tube 48 couples milk collection device 12 to vacuum pump 16. The term, "vacuum pump," refers to any device that provides subatmospheric pressure continuously, cyclically, or at least momentarily. Vacuum pump 16 is schematically illustrated to represent all types of vacuum pumps, examples of which include, but are not limited to, a diaphragm pump, a bellows pump, a piston pump, a reciprocating pump, a peristaltic pump, a positive displacement pump, a gear pump, a lobed rotor pump, a screw compressor, a scroll compressor, and a rotary vane pump.

The breast pump system's structure and operation can be further understood with additional definitions and explanations of some detailed features of the system. Nipple receptacle 32 has an inner curved wall surface 50, an outer curved wall surface 52, a proximate end 54 and a distal end 56. The nipple receptacle's tubular shape defines a longitudinal centerline 58 and nipple chamber 36. A minimum radial distance 60 exists between longitudinal centerline 58 and inner curved wall surface 50, wherein the minimum radial distance is measured perpendicular to centerline 58. Nipple receptacle 32 extends longitudinally in a forward direction 62 (parallel to centerline 58) from proximate end 54 to distal end 56. In some examples, nipple chamber 36 extends farther forward than distal end 56 of nipple receptacle 32; however, any part of nipple receptacle 32 that happens to extend farther forward than nipple chamber 36 is considered an extension beyond distal end 56 and thus is not considered the receptacle's distal end 56 itself. In some examples, the most forward point of nipple chamber 36 is at a domed concave surface 64 on fluid exchanger 26. Surface 64 being domed rather than flat makes fluid exchanger 26 easier to clean after fluid exchanger 26 is separated from breast receiver 22.

When breast receiver 22 and valve 28 are attached to fluid exchanger 26, the resulting assembly produces various fluid passages, chambers and sealing interfaces. Upon disassembly, the passages, chambers and sealing interfaces become more open for easier cleaning and sanitizing. Examples of such passages, chambers and sealing interfaces include charging chamber 46, nipple chamber 36, a milk passage 66 for conveying milk 14 from nipple chamber 36 to charging chamber 46, a valve outlet 68 that periodically discharges discrete volumes of milk 14 to storage chamber 42, an air duct 70 that connects suction tube 48 in fluid communication with charging chamber 46, a primary sealing interface 72, and a secondary sealing interface 74.

Figure 2:
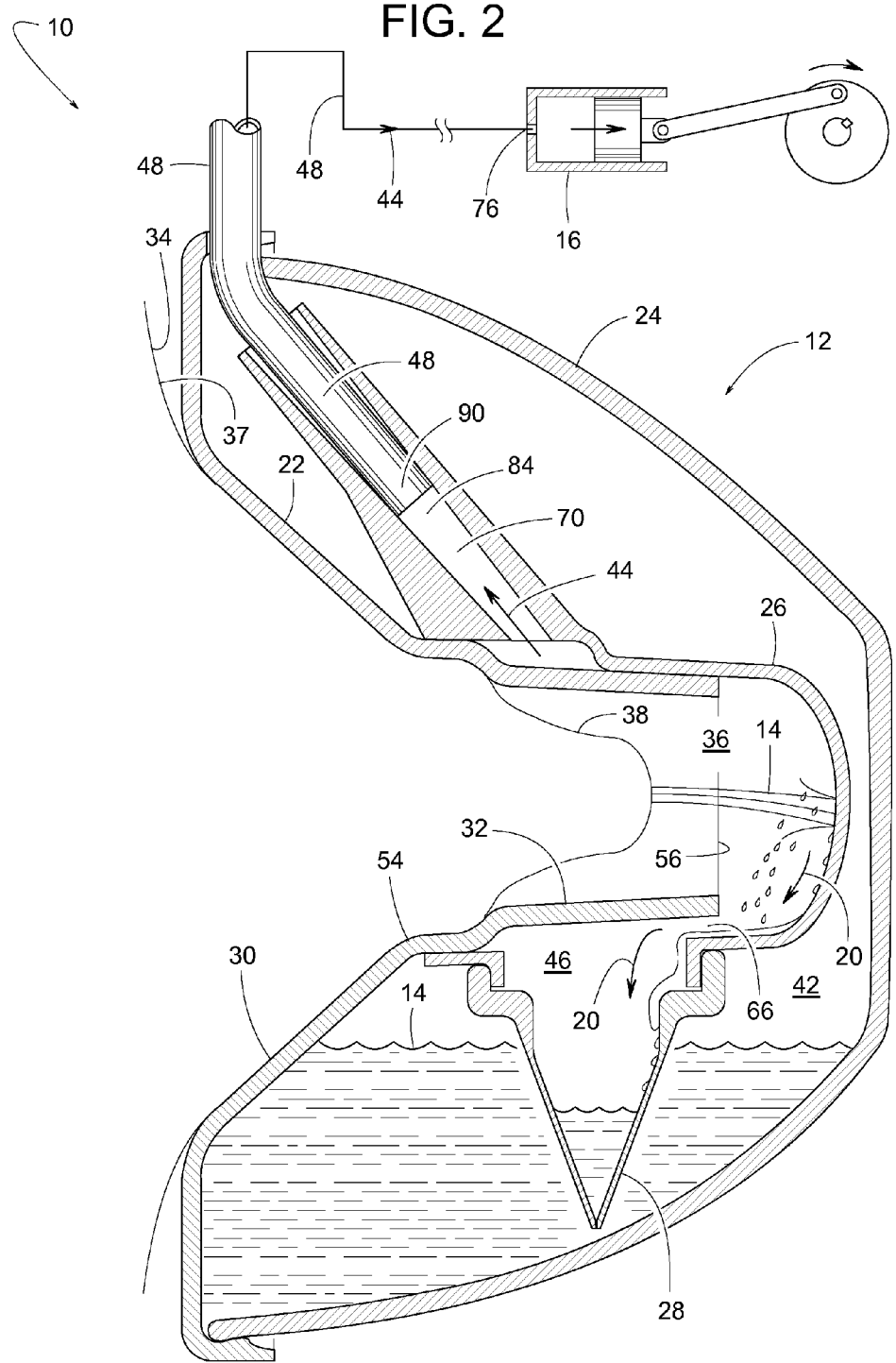
FIG. 2 is a combination schematic diagram and cross-sectional side view similar to FIG. 1 but showing the milk collection device as part of an example breast pump system.
Figure 15:
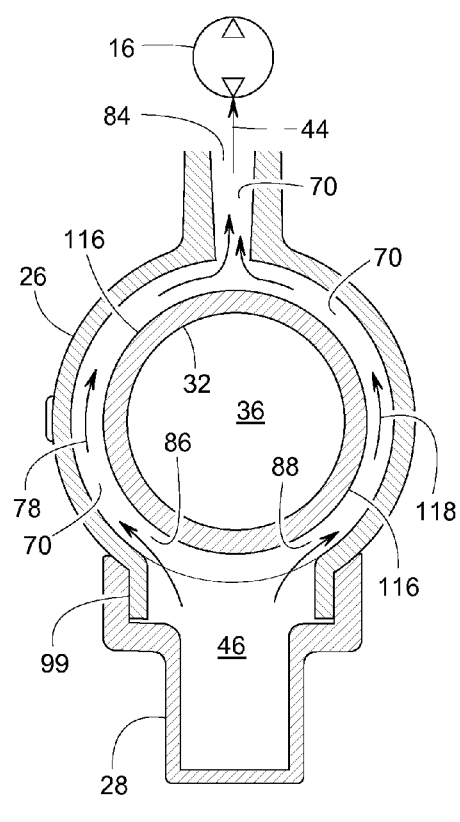
FIG. 15 is a cross-sectional view similar to FIG. 10 but showing an airflow pattern during a negative pressure period (first period).

In some examples, system 10 operates in an alternating manner of suction periods and pressurized periods. During suction periods, as shown in FIGS. 2 and 15, vacuum pump 16 applies suction or air at subatmospheric pressure to a remote end 76 of suction tube 48. At least some of the vacuum reaches nipple chamber 36 to draw milk expressed from nipple 38. The expressed milk 14 flows from nipple chamber 36, flows through milk passage 66, and collects at the bottom of charging chamber 46. The negative air pressure produced by vacuum pump 16 creates a first current of air 78 (FIG. 15) that effectively moves from nipple chamber 36 and effectively flows in series through milk passage 66, through charging chamber 46, through air duct 70 (FIGS. 9, 10, 15 and 16), through suction tube 48, and to vacuum pump 16. The terms, "effectively moves" and "effectively flows" means that there is some air movement from an upstream point toward a downstream point, but the air at the upstream point will not necessarily reach the downstream point, due to the travel distance and/or other flow constraints.

Figure 3:
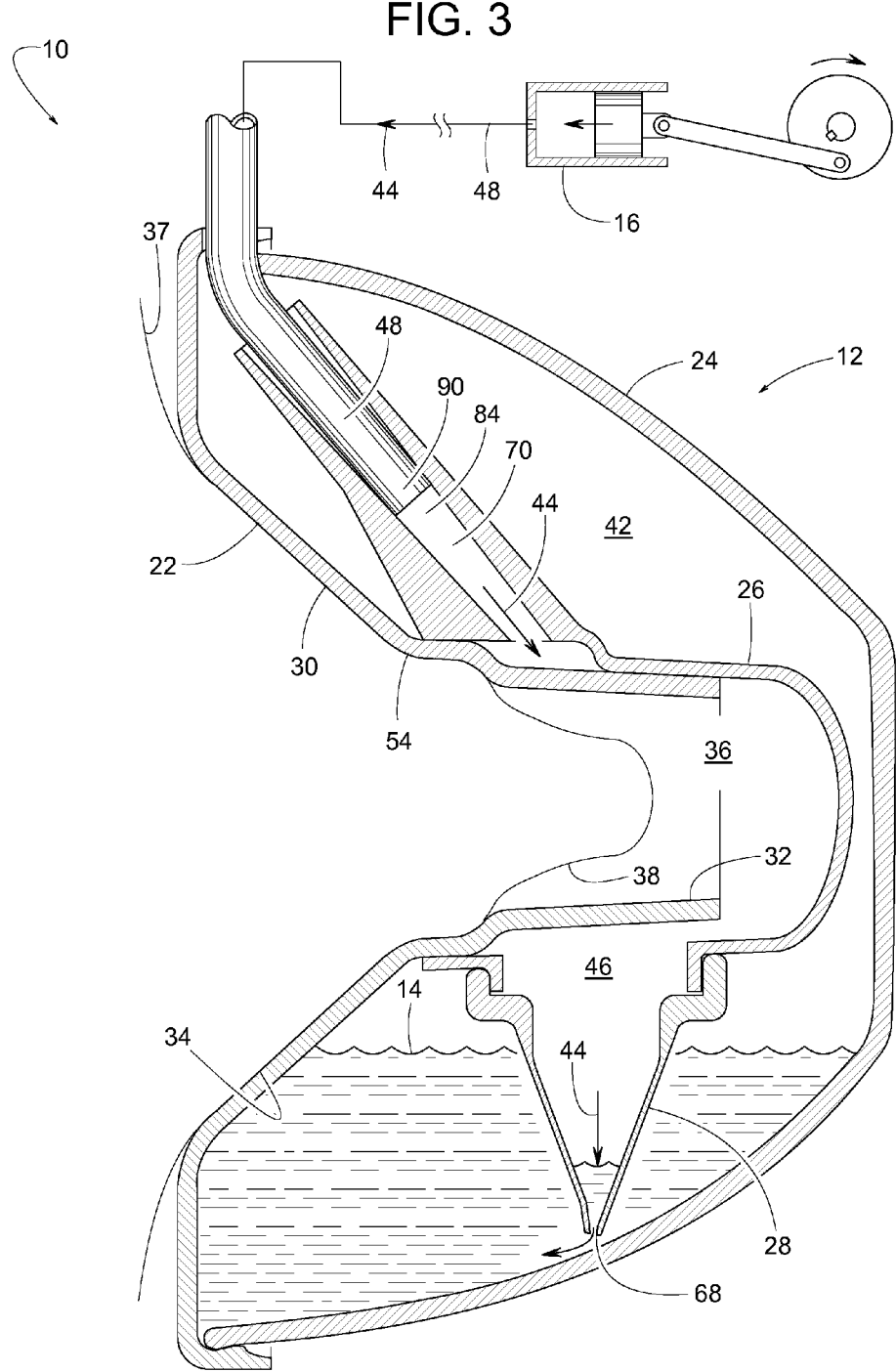
FIG. 3 is a view similar to FIG. 2 but showing the system during a positive pressure period rather than a suction pressure period.
Figure 4:
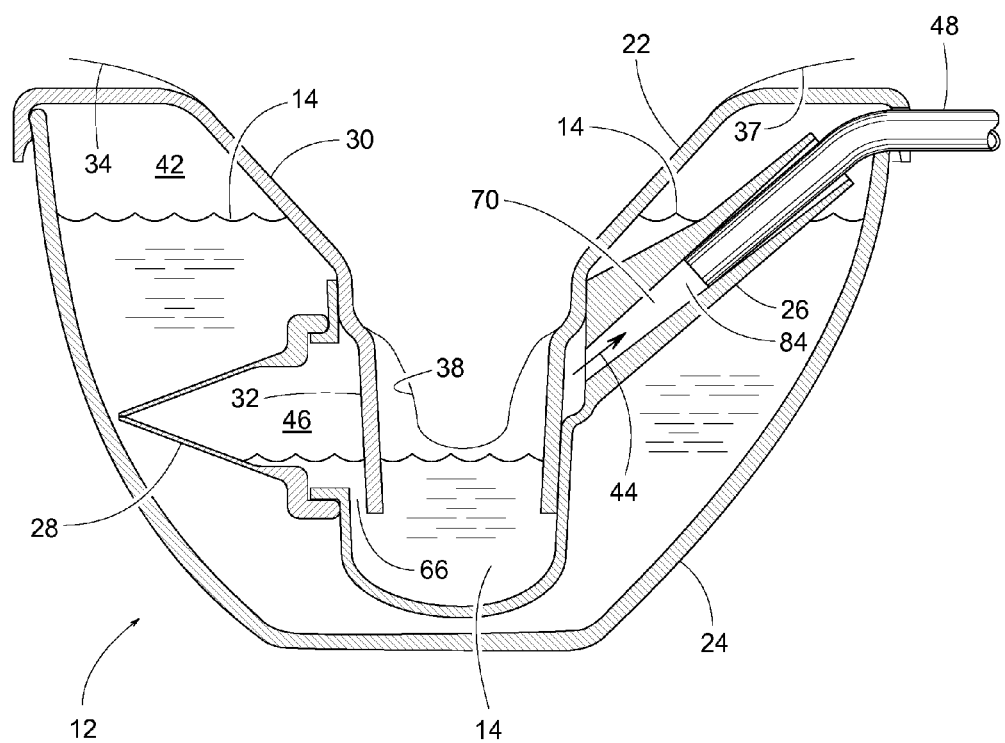
FIG. 4 is a cross-sectional side view of the milk collection device shown in FIGS. 1-3, but showing the device fully tipped over and pointed down.
Figure 16:
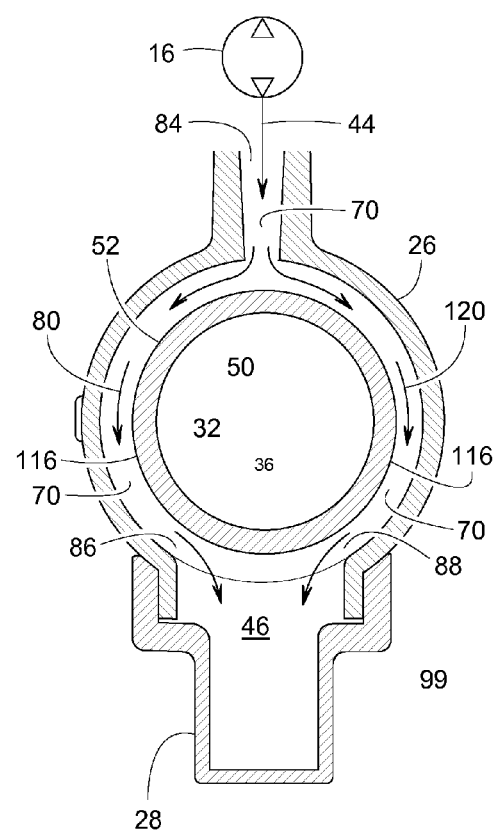
FIG. 16 is a cross-sectional view similar to FIG. 15 but showing an airflow pattern during a positive pressure period (second period).

During pressurized periods, as shown in FIGS. 3 and 16, vacuum pump 16 applies positive air pressure to suction tube 48. The positive pressure creates a second current of air 80 that effectively flows in series through suction tube 48, through air duct 70, through milk passage 66, and into nipple chamber 36. The air pressure in charging chamber 46 forces milk 14 (collected during the previous suction period) from charging chamber 46, down through valve 28, and into storage chamber 42. The air pressure in nipple chamber 36 allows breast 34 to relax prior to the next suction period.

The alternating cycle of suction and pressure is repeated for as long as desired or until storage chamber 42 is filled to some predetermined capacity. Upon completion of the pumping process, any suitable means can be used for transferring collected milk from storage chamber 42 to a bottle or to some other convenient storage container. One example method for transferring milk 14 from storage chamber 42 is to pull suction tube 48 out from within an opening 82 (FIG. 5) between breast receiver 22 and outer shell 24, and then pour collected milk 14 out through opening 82. Another method is to turn milk collection device 12 over (e.g., FIG. 4), remove breast receiver 22 from outer shell 24, and simply pour milk 14 out from shell 24.

Although FIG. 4 is referred to illustrate means for emptying milk 14 collected in storage chamber 42, the primary purpose of FIG. 4 is to show how well device 12 tolerates a completely tipped-over condition while still preventing milk 14 from backflowing into suction tube 48. Device 12 has three features that prevent milk backflow. One, in the tipped-over position, air duct 70 remains elevated above milk passage 66. Two, a circumferential seal 74 (FIG. 12) exists between air duct 70 and milk 14 in nipple chamber 36. Three, air duct 70 connects to charging chamber 46 at two spaced apart openings 86 and 88 (see FIG. 15 and the explanation referencing FIGS. 17, 18 and 19)

Preventing milk 14 from entering suction tube 48 is important for several reasons. Milk droplets or even a milk film trapped inside a narrow suction tube can be very difficult to thoroughly clean and sanitize. If left unclean, the trapped milk might contaminate future milk collections. Also, if milk in suction tube 48 migrates into vacuum pump 16, the milk can be even more difficult to remove and can possibly damage or destroy pump 16. Tolerating such unsanitized conditions is generally unheard of in the fields of medicine and food processing.

Figure 6:
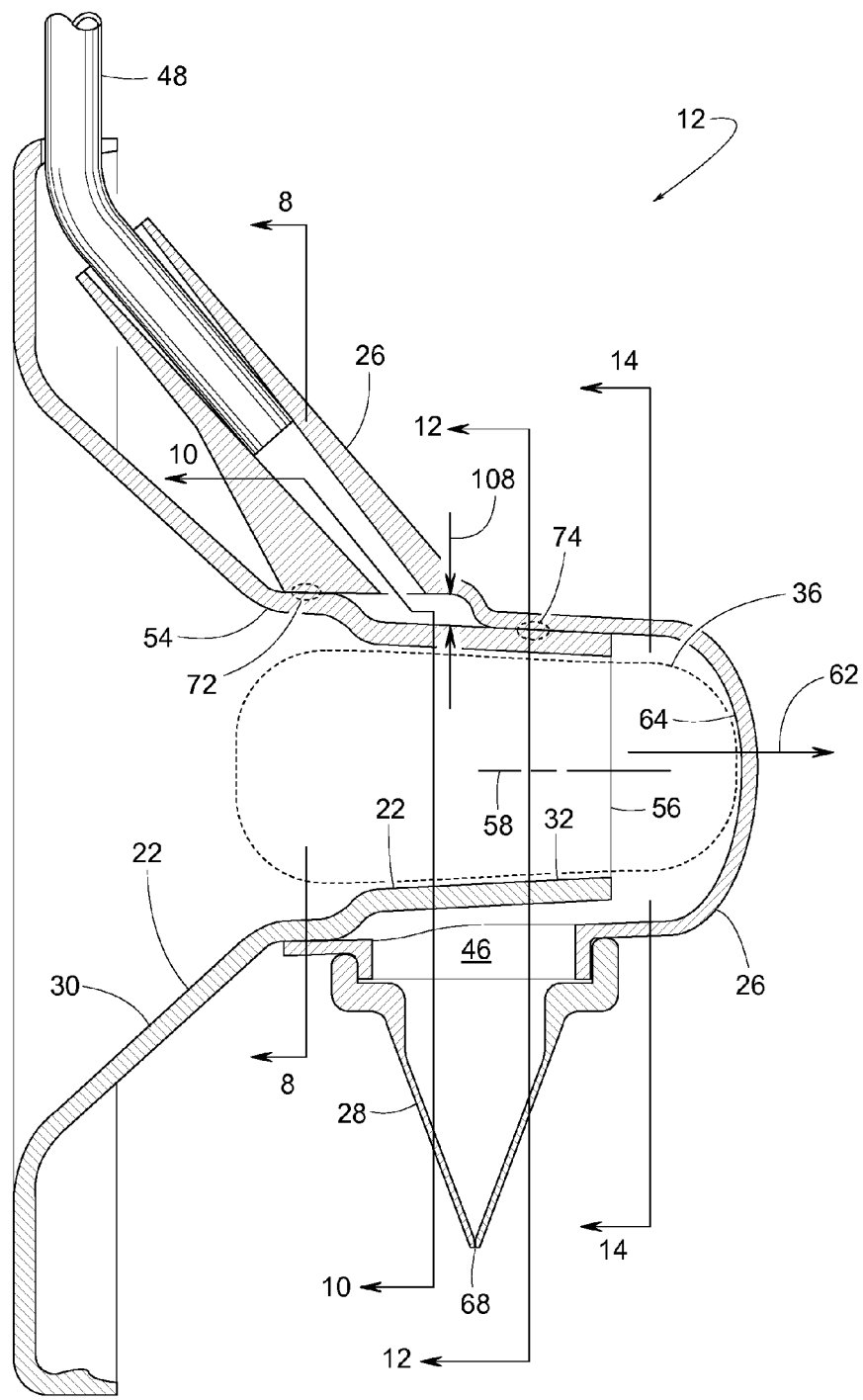
FIG. 6 is a cross-sectional view similar to FIG. 1 but with the outer shell omitted.
Figure 7:
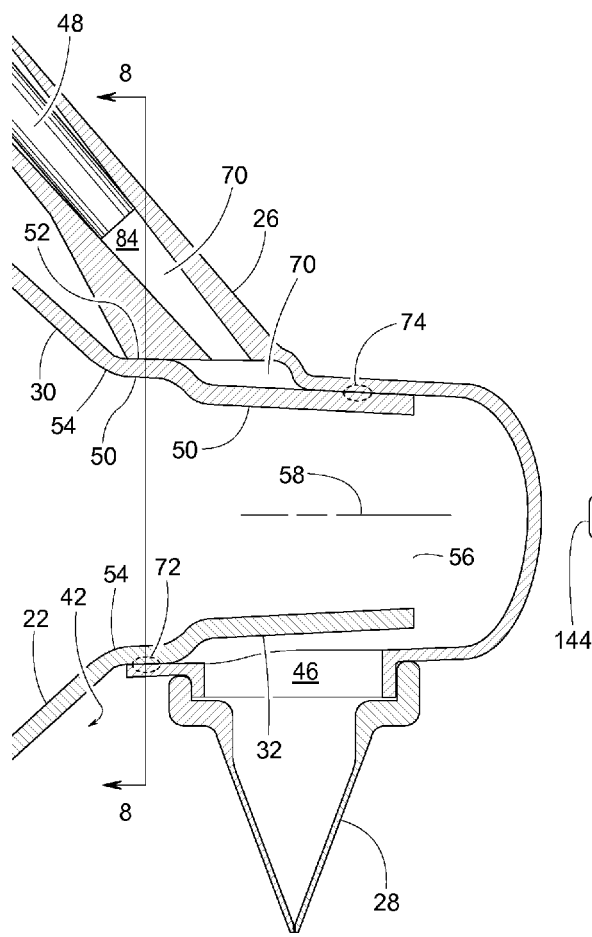
FIG. 7 is a cross-sectional view showing a portion of FIG. 6.
Figure 8:
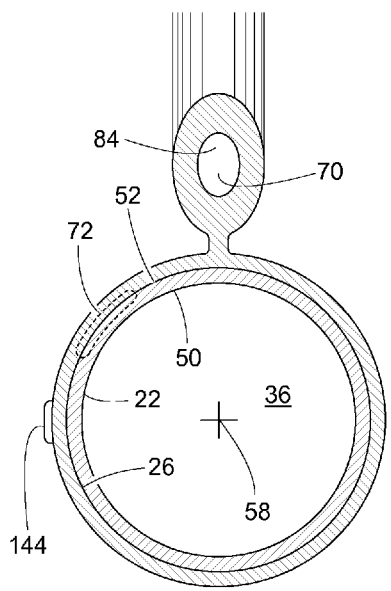
FIG. 8 is a cross-sectional view taken along line 8-8 of FIG. 7.

FIG. 6 serves as somewhat of an index drawing for a subsequent series of cross-sectional views. The views in the series are shown in sets of two and are identified as FIGS. 7-8, FIGS. 9-10, FIGS. 11-12, and FIGS. 13-14. FIGS. 7-8 show primary sealing interface 72 between an outer diameter of breast receiver 22 and an inner diameter of fluid exchanger 26. Primary sealing interface 72 is a relatively tight seal that extends 360 degrees circumferentially around centerline 58 to isolate localized pressure or vacuum within charging chamber 46 while the surrounding storage chamber 42 is at atmospheric pressure. In some examples, to ensure a positive seal, interface 72 tapers at 3-degrees in a lengthwise direction with reference to centerline 58.

FIGS. 9-10 show one example of air duct 70 connecting vacuum tube 48 in fluid communication with charging chamber 46. In this example, air duct 70 comprises a supply port 84 at a connection end 90 of suction tube 48, a first opening 86 at charging chamber 46, and a second opening 88 at charging chamber 46. To connect tube 48 to supply port 84, connection end 90 of suction tube 48 press-fits into a tapered bore 92 of fluid exchanger 26. A fork 94 (e.g., one path leading to two) in air duct 70 connects supply port 84 in fluid communication with openings 86 and 88. Features 84, 86 and 88 of FIG. 10 correspond respectively to points 84', 86' and 88' of FIG. 18. Features 84, 86 and 88 of FIG. 10 also correspond respectively to points 84", 86" and 88" of FIG. 19.

To apply the "vacuum break" concept illustrated in FIGS. 17 and 18, fork 94 straddles nipple receptacle 32 so that openings 86 and 88 are spaced apart in a lateral direction 96 with the nipple receptacle longitudinal centerline 58 being laterally interposed between openings 86 and 88 (dimensions 98 and 100). In some examples, nipple receptacle 32 is flanked by openings 86 and 88, which means that the nipple's longitudinal centerline 58 is laterally between openings 86 and 88, as shown in FIG. 10. The spaced-apart distance and elevation of openings 86 and 88 can be increased by increasing the diameter of a flange 99 to which valve 28 is attached.

Still referring to FIG. 10, some examples of air duct 70 define a flow path 102 from supply port 84 to first opening 86, wherein a curved section of flow path 102 extends circumferentially an angular distance 104 of at least thirty degrees to avoid having to create an alternate flow path in front of or through nipple chamber 36. In some examples, at least one section 106 of flow path 102 lies within a radial gap 108 between fluid exchanger 26 and the nipple receptacle's outer curved wall surface 52. Upon disassembling device 12 to its disassembled cleaning state (FIG. 5), section 106 of flow path 102 is split apart, which makes flow path 102 and air duct 70 much more accessible for cleaning.

FIGS. 11 and 12 show secondary sealing interface 74 radially between fluid exchanger 26 and the nipple receptacle's outer curved wall surface 52. Secondary sealing interface 74 provides a barrier that prevents milk 14 from flowing directly from nipple chamber 36 to air duct 70. FIG. 11 shows air duct 70 being between primary sealing interface 72 and secondary sealing interface 74.

Primary sealing interface 72 is the more critical seal of the two because primary sealing interface 72 is subjected to an appreciable pressure differential between supply port 84 and storage chamber 42. Secondary sealing interface 74, however, is not as critical because the pressure differential between supply port 84 and nipple chamber 36 is nearly zero. Consequently, in some examples, primary sealing interface 72 is made to be a tighter seal than secondary sealing interface 74. In other words, when breast receiver 22 is snugly inserted into fluid exchanger 26, the radial forces at primary sealing interface 72 is greater than that at secondary sealing interface 74.

It can be important to have primary sealing interface 72 be the dominant seal because when breast receiver 22 is inserted into fluid exchanger 26, something has to "bottom out" first to stop the relative insertion movement of breast receiver 22 into fluid exchanger 26. If secondary sealing surface 74 or distal end 56 abutting domed surface 64 were to be the first parts to bottom out, that might leave some radial clearance or leak path at primary sealing interface 72. Intentionally making primary sealing interface 72 be the first to bottom out, loosens the manufacturing tolerances at other near bottom-out locations, thus increasing assembly reliability, reducing tooling costs, and simplifying manufacturing.

FIGS. 13 and 14 show milk passage 66 between charging chamber 46 and nipple chamber 36. FIGS. 14 and 5 show how an irregular shaped upper flange 110 of valve 28 serves as a means for "clocking" or rotationally aligning valve 28 to fluid exchanger 26. Such alignment can be important to avoid interference between a lower end 112 of valve 28 and outer shell 24. For instance, if valve 28 were rotated ninety degrees (about a vertical axis 114) from the position shown in FIG. 1, the valve's lower end 112 might press up against outer shell 24, whereby outer shell 24 might hold valve 28 open and prevent it from closing.

FIGS. 15 and 16 illustrate an example breast pump method operating during a first suction period (FIGS. 2 and 15) and a second pressure period (FIGS. 3 and 16). FIG. 15 shows during the first period, directing first current of air 78 in a first curved upward direction circumferentially across a first outer convex wall surface 116 of nipple receptacle 32. FIG. 15 also shows during the first period, directing a third current of air 118 in a second curved upward direction circumferentially across the nipple receptacle's first outer convex wall surface 116. FIG. 16 shows during the second period, directing second current of air 80 in a first curved downward direction circumferentially across the nipple receptacle's first outer curved wall surface 116. FIG. 16 also shows during the second period, directing a fourth current of air 120 in a second curved downward direction circumferentially across the nipple receptacle's first outer curved wall surface 116, wherein nipple receptacle 32 is interposed between first current of air 78 and third current of air 118 during the first period, and nipple receptacle 32 is interposed between second current of air 80 and fourth current of air 120 during the second period.

FIGS. 17 and 18 illustrates the concept of a vacuum breaker as a means for preventing a liquid 122 from backflowing up to a suction source 124. Liquid 122 only reaches suction source 124 when both openings 86' and 88' are submerged in liquid 122, as shown in FIG. 17. If only one opening 86' is submerged and the other opening 88' is exposed to air 44, as shown in FIG. 18, air 44 readily supplies the volume drawn in by suction source 124. Through a given opening, air can flow about thirty times easier than water. Consequently, only a slight pressure differential is needed for air 44 to rush through opening 88' to suction source 124. That slight pressure differential creates only a slight pressure head 126 that is unable to lift liquid 122 from opening 86' to suction source 124.

FIG. 19 provides another example of illustrating a vacuum breaker concept. This example involves the use of a residential water line 128, an outdoor faucet 130, a simplified vacuum breaker 132, and a garden hose 134 partially submerged in a bucket 136 of contaminated water 138. In this example, if unusual adverse conditions create a vacuum in water line 128, clean outdoor air 44 rather than contaminated water 138 will be drawn into water line 128.

FIGS. 20, 21 and 22 show various design modifications. FIG. 20 shows an altered milk passage 66' created by a beveled edge 140 at the end of a nipple receptacle 32'. FIG. 21 shows an altered milk passage 66" created by a notched edge 142 at the end of a nipple receptacle 32". FIG. 22 shows that a stubbier fluid exchanger 26' and a less protruding outer shell 24' can be used when air duct 4 curves around the sides of the nipple receptacle rather than in front of it. The stubbier fluid exchanger 26' also reduces the effective volume of charging chamber 46, which can be beneficial when using certain low displacement vacuum pumps.

For further clarification, the term, "suction tube" refers to any conduit having a tubular wall of sufficient thickness, stiffness, and/or strength to convey air at subatmospheric pressure. In some examples, suction tube 48 is more flexible than outer shell 24, breast receiver 22, and/or fluid exchanger 26. Such tube flexibility makes tube 48 easier to use and fit to fluid exchanger 26. The term, "coupled to" refers to two members being connected either directly without an intermediate connecting piece or being connected indirectly via an intermediate connecting piece between the two members. The term, "coupled to" encompasses permanent connections (e.g., bonded, welded, etc.), seamless connections (e.g., the two members are of a unitary piece), and separable connections. The term, "opening" of a fluid pathway refers to a cross-sectional area through which fluid is directed to flow in a direction generally perpendicular to the area as guided by the fluid pathway. The term, "radial gap" refers to clearance as measured in a direction perpendicular to longitudinal centerline 58. The terms, "negative pressure," "subatmospheric pressure," and "vacuum" all refer to a pressure that is less than atmospheric pressure. The term, "positive pressure," refers to a pressure that is greater than atmospheric pressure. Storage chamber 42 is not necessarily for long term storage but rather for collecting and temporarily storing milk 14 as the lactating woman is expressing milk. In some examples, milk collection device 12 includes a slot-and-key 144 alignment feature (FIG. 8) that establishes a certain desired rotational alignment (about longitudinal centerline 58) between fluid exchanger 26 and breast receiver 22.

Although the invention is described with respect to a preferred embodiment, modifications thereto will be apparent to those of ordinary skill in the art. The scope of the invention, therefore, is to be determined by reference to the following claims:

The invention claimed is:

1. A breast pump system usable by a lactating woman for collecting milk, the breast pump system comprising:
   an outer shell;
   a breast receiver coupled to the outer shell, the breast receiver comprising a breast guide and a nipple receptacle;
   the breast guide being adapted to engage a breast of the lactating woman;
   the nipple receptacle being of a tubular shape and having an inner curved wall surface, an outer curved wall surface, a proximate end and a distal end; the proximate end being adjacent to the breast guide, the inner curved wall surface defining a nipple chamber extending from the proximate end to at least the distal end, the nipple chamber being adapted to receive a nipple of the breast, the nipple receptacle defining a longitudinal centerline, the nipple receptacle defining a forward direction that is parallel to the longitudinal centerline, the nipple receptacle having a minimum radial distance from the longitudinal centerline to the inner curved wall surface of the nipple receptacle, the minimum radial distance being perpendicular to the longitudinal centerline, the forward direction pointing away from the breast when the breast is engaging the breast guide, the nipple receptacle extending in the forward direction from the proximate end at the breast guide;
   a storage chamber being defined between the outer shell and the breast receiver;
   a fluid exchanger coupled to the nipple receptacle;
   a valve;
   a charging chamber defined within at least one of the fluid exchanger and the valve, the charging chamber being connected in fluid communication with the nipple chamber, the valve connecting the charging chamber in at least momentary fluid communication with the storage chamber;
   a suction tube having a connection end coupled to the fluid exchanger and a remote end extending beyond the storage chamber, the suction tube being more flexible than at least one of the outer shell, the breast receiver, and the fluid exchanger;
   an air duct connecting the connection end of the suction tube in fluid communication with the charging chamber, the air duct defining a supply port adjacent to the connection end of the suction tube, the air duct defining a first opening adjacent to both the nipple receptacle and the charging chamber, the air duct defines a flow path between the supply port and the first opening, and the flow path extends circumferentially at least thirty degrees around both the longitudinal centerline and the outer curved wall surface of the nipple receptacle; and
   the outer shell, the breast receiver and the fluid exchanger being selectively positionable as a unit to a predetermined orientation such that when the unit is in the predetermined orientation, the longitudinal centerline is horizontal, the longitudinal centerline extends over at least a portion of the charging chamber, the connection end of the suction tube is above the longitudinal centerline, and the nipple chamber extends farther forward than the first opening of the air duct by a horizontal distance that is greater than the minimum radial distance between the longitudinal centerline and the inner curved wall surface of the nipple receptacle.

2. The breast pump system of claim 1, wherein the air duct further defines a second opening adjacent to the charging chamber, the first opening and the second opening being spaced apart such that the longitudinal centerline of the nipple receptacle is interposed, with respect to a lateral direction, between the first opening and the second opening, wherein the lateral direction is horizontal and perpendicular to the longitudinal centerline when the unit is in the predetermined orientation.

3. The breast pump system of claim 1, wherein at least one section of the flow path lies within a radial gap between the fluid exchanger and the outer curved wall surface of the nipple receptacle.

4. The breast pump system of claim 3, wherein the fluid exchanger and the nipple receptacle are selectively configured in an assembled operating state and a disassembled cleaning state, the nipple receptacle engaging the fluid exchanger in the assembled operating state, the nipple receptacle disengaging the fluid exchanger in the disassembled cleaning state, the air duct at the at least one section of the flow path being intact in the assembled operating state, the air duct at the at least one section of the flow path being split apart in the disassembled cleaning state.

5. The breast pump system of claim 1, wherein at least one of the nipple receptacle and the fluid exchanger includes a domed concave surface facing a rearward direction toward the nipple chamber, the rearward direction being opposite of the forward direction, the domed concave surface being interposed between the nipple chamber and the outer shell.

6. The breast pump system of claim 1, further comprising:
   a primary sealing interface between the fluid exchanger and the outer curved wall surface of the nipple receptacle; and
   a secondary sealing interface being between the fluid exchanger and the outer curved wall surface of the nipple receptacle, the secondary sealing interface being farther forward than the primary sealing interface, the air duct being interposed between the primary sealing interface and the secondary sealing interface, and the primary sealing interface providing a tighter seal than the secondary sealing interface.

7. A breast pump system usable by a lactating woman for collecting milk, the breast pump system comprising:
   an outer shell;

a breast receiver coupled to the outer shell, the breast receiver comprising a breast guide and a nipple receptacle;

the breast guide being adapted to engage a breast of the lactating woman;

the nipple receptacle being of a tubular shape and having an inner curved wall surface, an outer curved wall surface, a proximate end and a distal end; the proximate end being adjacent to the breast guide, the inner curved wall surface defining a nipple chamber extending from the proximate end to at least the distal end, the nipple chamber being adapted to receive a nipple of the breast, the nipple receptacle defining a longitudinal centerline, the nipple receptacle defining a forward direction that is parallel to the longitudinal centerline, the nipple receptacle having a minimum radial distance from the longitudinal centerline to the inner curved wall surface of the nipple receptacle, the minimum radial distance being perpendicular to the longitudinal centerline, the forward direction pointing away from the breast when the breast is engaging the breast guide, the nipple receptacle extending in the forward direction from the proximate end at the breast guide;

a storage chamber being defined between the outer shell and the breast receiver;

a fluid exchanger coupled to the nipple receptacle;

a valve;

a charging chamber defined within at least one of the fluid exchanger and the valve, the charging chamber being connected in fluid communication with the nipple chamber, the valve connecting the charging chamber in at least momentary fluid communication with the storage chamber;

a suction tube having a connection end coupled to the fluid exchanger and a remote end extending beyond the storage chamber, the suction tube being more flexible than at least one of the outer shell, the breast receiver, and the fluid exchanger;

a valve connecting the charging chamber in at least momentary fluid communication with the storage chamber; and an air duct connecting the connection end of the suction tube in fluid communication with the charging chamber; the air duct defining a supply port adjacent to the connection end of the suction tube, the air duct defining a first opening adjacent to the charging chamber, the air duct defining a second opening adjacent to the charging chamber, the first opening being spaced apart from the second opening, the supply port being in fluid communication with both the first opening and the second opening.

8. The breast pump system of claim 7, wherein the outer shell, the breast receiver and the fluid exchanger are selectively positionable as a unit to a predetermined orientation such that when the unit is in the predetermined orientation, the longitudinal centerline is horizontal, the longitudinal centerline extends over at least a portion of the charging chamber, the supply port of the fluid exchanger is above the longitudinal centerline, and the nipple chamber extends farther forward than both the first opening and the second opening of the air duct.

9. The breast pump system of claim 7, wherein the air duct includes a fork that connects the supply port in fluid communication with the first opening and the second opening, and the fork straddles the nipple receptacle.

10. The breast pump system of claim 7, wherein the air duct defines a flow path between the supply port and the first opening, and at least one section of the flow path lies within a radial gap between the fluid exchanger and the outer curved wall surface of the nipple receptacle.

11. A breast pump system usable by a lactating woman for collecting milk, the breast pump system comprising:

an outer shell;

a breast receiver coupled to the outer shell, the breast receiver comprising a breast guide and a nipple receptacle;

the breast guide being adapted to engage a breast of the lactating woman;

the nipple receptacle being of a tubular shape and having an inner curved wall surface, an outer curved wall surface, a proximate end and a distal end, the proximate end being adjacent to the breast guide, the inner curved wall surface defining a nipple chamber extending from the proximate end to at least the distal end, the nipple chamber being adapted to receive a nipple of the breast, the nipple receptacle defining a longitudinal centerline, the nipple receptacle defining a forward direction that is parallel to the longitudinal centerline, the nipple receptacle having a minimum radial distance from the longitudinal centerline to the inner curved wall surface of the nipple receptacle, the minimum radial distance being perpendicular to the longitudinal centerline, the forward direction pointing away from the breast guide, the nipple receptacle extending in the forward direction from the proximate end of the nipple receptacle;

a storage chamber being defined between the outer shell and the breast receiver;

a fluid exchanger coupled to the nipple receptacle;

a valve;

a charging chamber defined within at least one of the fluid exchanger and the valve, the charging chamber being connected in fluid communication with the nipple chamber, the valve connecting the charging chamber in at least momentary fluid communication with the storage chamber;

a suction tube having a connection end coupled to the fluid exchanger and a remote end extending beyond the storage chamber, the suction tube being more flexible than at least one of the outer shell, the breast receiver, and the fluid exchanger;

a valve connecting the charging chamber in at least momentary fluid communication with the storage chamber; and an air duct connecting the connection end of the suction tube in fluid communication with the charging chamber, the air duct defining a supply port adjacent to the connection end of the suction tube, the air duct defining a first opening adjacent to the charging chamber, the supply port being in fluid communication with the first opening, the air duct defining a flow path between the supply port and the first opening, the flow path having a curved section that is curved at least partially around the nipple receptacle, the curved section lying within a radial gap between the fluid exchanger and the outer curved wall surface of the nipple receptacle, the curved section of the flow path being directly up against the outer curved wall surface of the nipple receptacle.

12. The breast pump system of claim 11, wherein the fluid exchanger and the nipple receptacle are selectively configured in an assembled operating state and a disassembled cleaning state, the nipple receptacle engaging the fluid exchanger in the assembled operating state, the nipple receptacle disengaging the fluid exchanger in the disassembled cleaning state, the curved section of the flow path being intact in the assembled operating state, the curved section of the flow path being split apart in the disassembled cleaning state.

13. The breast pump system of claim 11, wherein the outer shell, the breast receiver and the fluid exchanger are selectively positionable as a unit to a predetermined orientation such that when the unit is in the predetermined orientation, the longitudinal centerline is horizontal and extends over at least a portion of the charging chamber, and the air duct further defines a second opening adjacent to the charging chamber, the first opening and the second opening being spaced apart such that with respect to a lateral direction the nipple receptacle is flanked by the first opening and the second opening, wherein the lateral direction is horizontal and perpendicular to the longitudinal centerline when the unit is in the predetermined orientation.

14. The breast pump system of claim 11, wherein at least one of the nipple receptacle and the fluid exchanger includes a domed concave surface facing a rearward direction toward the nipple chamber, the rearward direction being opposite of the forward direction, the domed concave surface being interposed between the nipple receptacle and the outer shell.

15. The breast pump system of claim 11, further comprising:
a primary sealing interface between the fluid exchanger and the outer curved wall surface of the nipple receptacle; and
a secondary sealing interface being between the fluid exchanger and the outer curved wall surface of the nipple receptacle, the secondary sealing interface being farther forward than the primary sealing interface, the air duct being interposed between the primary sealing interface and the secondary sealing interface, and the primary sealing interface providing a tighter seal than the secondary sealing interface.

16. A breast pump method usable by a lactating woman for collecting milk, the breast pump method comprising:
a nipple receptacle encircling a nipple of the lactating woman;
during a first period, directing a first current of air in a first curved upward direction circumferentially across a first outer convex wall surface of the nipple receptacle; and
during a second period, directing a second current of air in a first curved downward direction circumferentially across the first outer curved wall surface of the nipple receptacle.

17. The breast pump method of claim 16, wherein the second current of air is pressurized at greater than atmospheric pressure, and the first current of air is at subatmospheric pressure.

18. The breast pump method of claim 16, further comprising:
during the first period, directing a third current of air in a second curved upward direction circumferentially across the first outer convex wall surface of the nipple receptacle; and
during the second period, directing a fourth current of air in a second curved downward direction circumferentially across the first outer curved wall surface of the nipple receptacle, wherein the nipple receptacle is interposed between the first current of air and the third current of air during the first period, and the nipple receptacle is interposed between the second current of air and the fourth current of air during the second period.

19. A breast pump system usable by a lactating woman for collecting milk, the breast pump system comprising:
an outer shell;
a breast receiver coupled to the outer shell, the breast receiver comprising a breast guide and a nipple receptacle;
the breast guide being adapted to engage a breast of the lactating woman;
the nipple receptacle being of a tubular shape defining a longitudinal centerline, the nipple receptacle having a nipple chamber that is elongate in a direction parallel to the longitudinal centerline, the nipple chamber being adapted to receive a nipple of the breast;
a storage chamber being defined between the outer shell and the breast receiver;
a fluid exchanger coupled to the nipple receptacle;
a valve;
a charging chamber defined within at least one of the fluid exchanger and the valve, the charging chamber being connected in fluid communication with the nipple chamber, the valve connecting the charging chamber in at least momentary fluid communication with the storage chamber; and
a domed concave surface facing into the nipple chamber, facing away from the outer shell, and the nipple chamber extending out to the domed concave surface.

20. The breast pump system of claim 19, wherein the longitudinal centerline intersects the domed concave surface.

21. The breast pump system of claim 19, wherein domed concave surface is on the fluid exchanger.

22. The breast pump system of claim 19, wherein the domed concave surface is on the nipple receptacle.

23. The breast pump system of claim 19, wherein the domed concave surface is spaced apart from the nipple receptacle.

* * * * *